United States Patent [19]
Böbel et al.

[11] Patent Number: 5,153,674
[45] Date of Patent: Oct. 6, 1992

[54] SEMICONDUCTOR PRODUCTION CONTROL AND/OR MEASURING UNIT

[75] Inventors: Friedrich Böbel, Uttenreuth; Norbert Bauer, Erlangen, both of Fed. Rep. of Germany

[73] Assignee: Fraunhofer Gesellschaft Zur Forderung der angewandt, Munich, Fed. Rep. of Germany

[21] Appl. No.: 652,150

[22] Filed: Feb. 7, 1991

[30] Foreign Application Priority Data

Sep. 7, 1990 [DE] Fed. Rep. of Germany ... 9012816[U]

[51] Int. Cl.⁵ .................... G01N 15/02; G01N 21/64
[52] U.S. Cl. .................... 356/336; 356/339; 250/458.1; 250/461.1
[58] Field of Search .............. 356/335–343, 356/317, 318, 301, 382; 250/574, 458.1, 461.1; 204/192.33, 298.32

[56] References Cited

U.S. PATENT DOCUMENTS

| | | | |
|---|---|---|---|
| 4,291,230 | 9/1981 | Heiss | 250/458.1 |
| 4,380,392 | 4/1983 | Karabegov et al. | 356/336 |
| 4,394,237 | 7/1983 | Donnelly et al. | 356/318 |
| 4,429,995 | 2/1984 | Goulas | 356/343 |
| 4,698,308 | 10/1987 | Ikeda | 250/458.1 |
| 4,745,285 | 5/1988 | Recktenwald et al. | 250/461.1 |
| 4,919,536 | 4/1990 | Komine | 356/338 |
| 4,948,259 | 8/1990 | Enke et al. | 356/382 |
| 4,986,654 | 1/1991 | Meijer et al. | 250/458.1 |

FOREIGN PATENT DOCUMENTS

| | | |
|---|---|---|
| 3901017 | 7/1990 | Fed. Rep. of Germany . |
| 2104650 | 7/1982 | United Kingdom . |
| 2189881 | 11/1987 | United Kingdom . |

OTHER PUBLICATIONS

Electro-optical products division ITT, "F4548 Spectroscopic Instrument", Rev. Mar. 1985.

*Primary Examiner*—Richard A. Rosenberger
*Assistant Examiner*—Hoa Pham
*Attorney, Agent, or Firm*—Ralph H. Dougherty

[57] ABSTRACT

A semiconductor production control and measuring unit for a two-dimensional detection and control of concentration and pressure distribution of process particles within a process chamber, which forms part of a semiconductor production device and in the interior of which a vacuum can be generated with the aid of a vacuum pump. A light fan source produces a substantially parallel light fan within the process chamber, the light fan penetrating the area of the process chamber which is to be examined with regard to concentration distribution or pressure distribution, the wavelength of the light emitted by the light fan source being so short that the process particle have imparted thereto an excitation energy sufficient for fluorescent radiation. A camera is disposed at an angle with respect to the light fan and it covers the area to be examined. In the spectral region of the fluorescent radiation of the process particles, the camera has a quantum efficiency which detects the fluorescent radiation. A processing device is connected to the camera and determines the two-dimensional concentration and pressure distribution of the process particles on the basis of the image signals received from the camera.

10 Claims, 1 Drawing Sheet

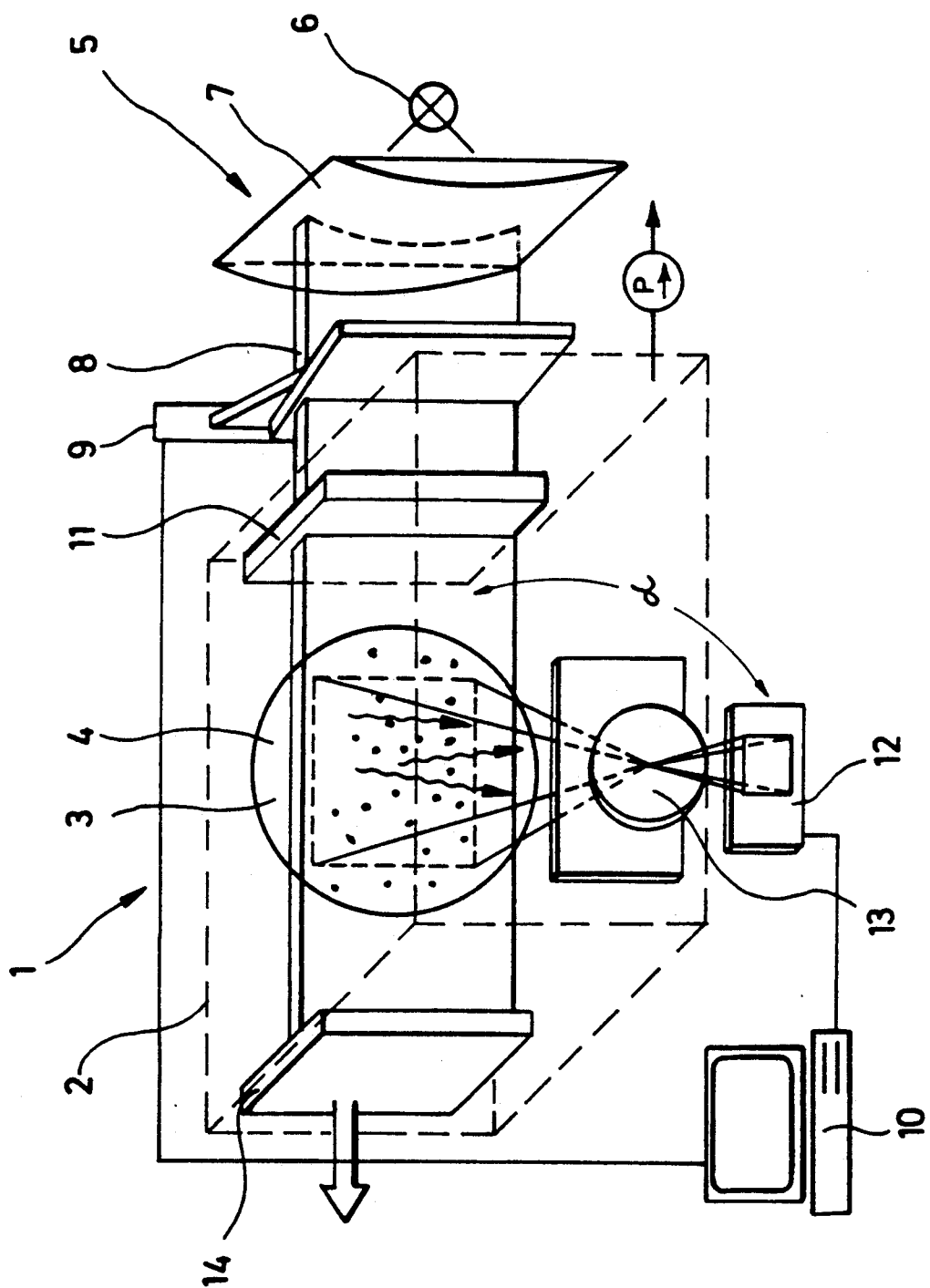

SEMICONDUCTOR PRODUCTION CONTROL AND/OR MEASURING UNIT

FIELD OF THE INVENTION

The present invention refers to a control and/or measuring unit for use in the field of semiconductor technology for carrying out a two-dimensional detection and/or control of concentration and/or pressure distributions of process particles within a process chamber of a semiconductor production device.

BACKGROUND OF THE INVENTION

In the case of most processes taking place in the field of semiconductor production technology, the knowledge of the locus-dependent pressure and concentration characteristics of the gases, vapors and plasmas or of the process particles in general is of decisive importance as far as process monitoring and process control are concerned. A point of special interest in case of these processes is the homogeneity of the particle concentration in the process atmosphere above the semiconductor structure to be produced.

It is known that the pressure values occurring within the process chamber during a semiconductor-structure coating process can be monitored by means of pressure gauges, the following pressure gauges being used depending on the pressure to be monitored or measured: heat-conduction vacuum gauges for the fine vacuum region; cold-cathode vacuum gauges for high vacuum up to and into ultrahigh vacuum region; hot-cathode ionization vacuum gauges for the fine vacuum region up to the extreme ultrahigh vacuum region as well as quadruple mass spectrometers. Such pressure gauges cannot be used for a two-dimensional detection of concentration and/or pressure distributions of process particles. Nor is it possible to detect by means of such pressure gauges the concentration of the particles participating in the coating process itself, since the particles to be measured are withdrawn from the process by the known pressure gauges described above, and which suck in the particles.

From the field of flame diagnosis, a fluorescence measuring method is known, in the case of which a high-power dye laser light source is used for exciting the flame gases to emit fluorescent radiation. On the basis of the fluorescent radiation emitted, it is then possible to carry out a two-dimensional pressure detection within the flame. The sensitivity of this fluorescent measuring method known from the field of flame diagnosis is several orders of magnitude lower than the sensitivity required for control and measuring methods in the field of semiconductor production. Furthermore, the high-powered dye laser light sources which are required for flame diagnosis and which are sold at a price of approximately $200,000 per unit are too uneconomic for most cases of use outside purely basic research.

European Patent EP-A2-0070523 discloses a control and measuring European unit for use in the field of semiconductor production for detecting the concentration or the pressure of process particles at a location examined within the process chamber, within which a vacuum can be created, comprising a light beam source used for producing a light beam within the process chamber, the light beam penetrating an area of the process chamber which is to be examined and the wavelength of the light emitted by the light beam source being so short that the process particles have imparted thereto an excitation energy which suffices for fluorescent radiation, a pick-up device in the form of a detector, which is arranged such that its detection area is disposed at right angles to the light beam and the spectral sensitivity of which is chosen such that, in the spectral region of the fluorescent radiation of the process particles, said spectral sensitivity has a quantum efficiency which suffices for detecting the fluorescent radiation, and an integrator, which is connected to the detector and which is used for determining concentrations or pressures of the process particles at the location examined. However, the European reference does not disclose any information with regard to the concept of fanning the light so as to produce a substantially parallel light fan within the process chamber, nor does it disclose any information with regard to the use of a camera for planar detection of the fluorescent radiation within the process chamber for producing thus a two-dimensional image of the concentration distribution or of the pressure distribution of process particles within the process chamber.

In the case of the subject matter of European application EP-A2-0070523, it is, additionally, necessary to use high-powered, expensive Excimer laser units instead of comparatively low-powered laser light source which is used in the present invention. EP-A2-0070523 especially fails to refer in any way to the importance of the low pressure within the process chamber with regard to the use of low powered laser light sources or other light sources. For the purpose of full disclosure of the technological background of the present invention, reference is made to the following publications: DE-A1-3901017, GB-A-2104650; GB-A-2189881 and US-A-4394237.

The present invention solves the problem of creating a semiconductor production control and/or measuring unit for a two-dimensional detection and/or control of concentration and/or pressure distributions of process particles within a semiconductor production device.

The present invention is a semiconductor production control and/or measuring unit for a two-dimensional detection and/or control of concentration and/or pressure distributions of process particles within a process chamber, which forms part of a semiconductor production device and in the interior of which a vacuum can be generated with the aid of a vacuum pump means, the control and/or measuring unit comprising the following features:

a light fan source used for producing a substantially parallel light fan within the process chamber, the light fan penetrating the area of the process chamber which is to be examined with regard to concentration distribution and/or pressure distribution and the wavelength of the light fan source being so short that the process particles have imparted thereto an excitation energy which suffices for fluorescent radiation;

a camera which is arranged such that its camera direction is disposed at an angle with respect of the light fan and that it covers the area to be examined, the spectral sensitivity of the camera being selected such that, in the spectral region of the fluorescent radiation of the process particles, the camera has a quantum efficiency which suffices for detecting fluorescent radiation; and a processing device, which is connected to the camera and which determines the two-dimensional concentration and/or pressure distribution of the process particles on the basis of the image signals received from the camera.

The present invention is based on the finding that, in spite of the high sensitivity required for the purpose of semiconductor production technology, it is possible to use the fluorescence measuring method, which, in the field of flame diagnosis, can only be realized with low sensitivity, since the problems of quenching and of Mie scattering by dust particles, which reduce the sensitivity of the fluorescence measuring method in the case of flame diagnosis, do not arise under the process conditions of semiconductor production technology. In view of the fact that the interfering effects of quenching and of Mie scattering do not occur, or occur only to an negligible extent, under the skeleton conditions of semiconductor technology, the light source used can be a light source of low power, e.g. a photoflash bulb. The price of such a light source is several orders of ten lower than the price of the dye laser light sources used in the field of flame diagnosis. It follows that the unit according to the present invention can also be realized at a reasonable price.

BRIEF DESCRIPTION OF THE DRAWINGS

Other objects and advantages will be apparent from the following description when taken in conjunction with the accompanying drawing, in which:

The single figure shows an embodiment of the semiconductor production control and/or measuring unit according to the present invention.

DESCRIPTION OF THE PREFERRED EMBODIMENT

In the figure, reference numeral 1 refers to the semiconductor production device in its entirety, the semiconductor production device having a semiconductor wafer 3 arranged within its process chamber 2.

The semiconductor wafer 3 is exposed to a directed or non-directed incidence of process particles 4. Within the process chamber 2, there is a vacuum of typically $10^{-2}$ to $10^{-7}$ mbar, which is generated by a vacuum pump means. For extreme cases of use, ultra high vacuum ranges of up to $10^{-11}$ mbar are achievable as well.

Outside of the process chamber 2, a light fan source 5 is arranged. The light fan source 5 includes a photoflash bulb 6, which is followed in the light path by a fanning optics 7 provided with an integrated slit diaphragm for producing a narrow light fan or light section defined by parallel light rays. The wavelength of the light emitted by the photoflash bulb 6 is chosen such that it is so short that the process particles have imparted thereto an excitation energy which suffices for fluorescent radiation. The excitation energies are typically within the ultraviolet region.

A beam splitter 8, which is arranged subsequent to the fanning optics 7 in the light path, directs part of the light fan onto a line-shaped CCD sensor 9, which is connected to an image processing device 10 at its output side. The light fan enters the process chamber through a first window 11, and in the process chamber it penetrates the area, which is to be examined with regard to concentration distribution and/or pressure distribution, above the semiconductor wafer 3. The first window 11 is a high-vacuum resistant quartz glass window, which has a high transmittance for ultraviolet light and which is resistant to the chemical conditions within the process chamber 2.

Outside of the process chamber, a camera 12 is arranged, which serves to detect the fluorescent radiation within the process chamber 2, the fluorescent radiation being emitted by the process particles excited by the light fan. The camera 12 is a highly responsive, two-dimensional camera. In the preferred embodiment, this camera is an MCP (micro channel plate)—amplified CCD camera having a sufficiently high quantum efficiency in the spectral region of the fluorescent radiation. The camera 12 is arranged at an angle $\alpha$ with respect to the light fan. In order to avoid a numeric correction of otherwise occurring projection distortions, the angle $\alpha$ between the camera direction of the camera 12 and the light fan will normally and preferably be a right angle.

The camera 12 includes a suitable optical system by means of which the fluorescent radiation of the process particles can be imaged in the taking plane of the camera 12. The camera and the process chamber 2 have arranged between them a second window 13, which, too, permits high-vacuum sealing, which has a high transmittance with respect to the fluorescent wavelength and which is resistant to the chemical condition within the process chamber 2.

Window 13 advantageously can also consist of quartz glass. The quartz glass used for the windows 11, 13, 14 is preferably an UVGSFS glass (ultraviolet grade synthetic fused silica) optimized with regard to the ultraviolet region.

Alternatively, the lens of an optical system can be substituted for the second window 13.

Finally, the process chamber 2 can be closed by a third window 14 through which the light fan leaves the process chamber 2. As far as its properties and its structure are concerned, the third window 14 can be replaced by a light trap.

The camera 12 is connected to the image processing device 10 on its output side. The image processing device 10 determines the two-dimensional concentration and/or pressure distribution of the process particles on the basis of the image signals received from the camera, the image processing device taking into account the signals for the vertical intensity distribution of the light fan, which are produced by the line-shaped CCD sensor 9.

In view of the fact that the fluorescent radiation detected by the camera has a characteristic wavelength which depends on the respective type of particles, a two-dimensional detection of partial pressure distributions in gas mixtures, molecular mixtures and iron mixtures can be affected.

The unit of the present invention and the method of the present invention are based on the fluorescent scattering of light by particles of atomic size (atoms, ions, molecules). For a not excessively great incidence power I, the intensity $I_F$ radiated by the excited particles is proportional to the incident light power an to the particle number density $n(x,y)$, which is, in turn, proportional to the pressure (ideal gas equation).

$$I_F = n(x,y) I \frac{B_{12}}{B_{21} + B_{12}} \frac{A_{21}}{A_{21} + Q_{21}} \qquad (1)$$

$B_{12}$, $B_{21}$ and $A_{21}$ in this case are the Einstein coefficients and $Q_{21}$ describes the number of radiationless transitions per unit time ("quenching" rate), which are caused by molecular bombardment. In the case of conventional fields of use (e.g. flame diagnosis), the "quenching" rate is in most cases several orders of ten greater than $A_{21}$, i.e. the fluorescence intensity becomes very small in accordance with equation (1). In view of the fact that the number of molecular bombardments per unit time is directly proportional to the particle number density, radiationless transitions are no longer of any importance in the case of low-pressure applications, whereby the detection sensitivity is markedly increased. An additional important quantity in the field of fluorescence spectroscopy is the saturation intensity $I_{SAT}$. When I becomes much greater than $I_{SAT}$, the fluorescence intensity is given by $$I_F = n(x,y) \frac{B_{12}}{B_{12} + B_{21}} A_{21} \quad (2)$$

i.e., the radiation power measured is independent of the incident intensity and directly proportional to the particle number density $n(x,y)$. The smaller $I_{SAT}$ is, the less difficulties will have to be overcome in order to achieve this situation which is aimed at from the point of view of measuring practice. The saturation intensity is, however, proportional to the expression $(A_{21}+Q_{21})$, i.e., in this case, too, the use of the vacuum technique will have the effect that the saturation intensity is reduced by several orders of ten so that the validity range of equation (2) can readily be achieved with minor technical expenditure.

What is claimed is:

1. A semiconductor production control and/or measuring unit for a two-dimensional detection and/or control of concentration and/or pressure distributions of process particles within a low pressure process chamber (2), which forms part of a semiconductor production device (1) and in the interior of which a vacuum below $10^{-2}$ mbar can be generated with the aid of a vacuum pump means, said unit comprising:
    a low power light fan source (5) for producing a substantially parallel light fan within said process chamber (2), said light fan penetrating the area of the process chamber (2), which is to be examined with regard to concentration distribution and/or pressure distribution, the power of the low power light fan source and the wavelength of the light emitted by the low power light fan source (5) being chosen such that the process particles have imparted thereto an excitation energy causing a resonant fluorescent radiation;
    a camera (12) so arranged that its camera direction is disposed at an angle with respect to the light fan and that it covers the area to be examined, the spectral region of the fluorescent radiation of the process particles, said camera has a quantum efficiency which suffices for detecting said fluorescent radiation;
    a processing device (10) connected to said camera (12);
    a beam splitter (8), arranged subsequent to the light fan source (5) in the light path; and
    a line-shaped sensor (9) for detecting the intensity distribution of the light across the light fan, said sensor (9) being arranged in the light path of the light emitted by the beam splitter and being connected to the processing device (10) on its output side;
    wherein said processing device (10) determines the two-dimensional concentration and/or pressure distribution of the process particles on the basis of the image signals received from the camera (12) and on the basis of the intensity distribution detected by the line-shaped sensor (9).

2. A semiconductor production control and/or measuring unit according to claim 1, wherein the light fan source (5) comprises a photoflash bulb (6) and a slit diaphragm (7).

3. S semiconductor production control and/or measuring unit according to claim 1, wherein the light fan source (5) is provided with a laser light source of low power in comparison with the power of a dye laser light source.

4. A semiconductor production control and/or measuring unit according to claim 1, wherein
    the light fan source (5) is arranged outside of the process chamber (2), and
    the light fan is supplied to the process chamber (2) through a first window (11), which permits high-vacuum sealing which has a high transmittance with respect to the wavelength of the light emitted by the light fan source (5) and which is resistant to the chemical conditions within the process chamber (2).

5. A semiconductor production control and/or measuring unit according to claim 4, wherein the window (11, 13) consists of quartz glass.

6. A semiconductor production control and/or measuring unit according to claim 1, wherein
    the camera (12) is arranged outside of the process chamber (2), and
    said process chamber (2) and said camera (12) have arranged between them a second window (13), which permits high-vacuum sealing, which has a high transmittance with respect to the fluorescence wavelength and which is resistant to the chemical conditions within the process chamber (2).

7. A semiconductor production control and/or measuring unit according to claim 1, wherein the angle between the camera direction of the camera (12) an the light fan is approximately 90°.

8. A semiconductor production control and/or measuring unit according to claim 1, wherein the camera is a CCD camera (12).

9. A semiconductor production control and/or measuring unit according to claim 8, wherein the CCD camera is an MCP (micro channel plate) - amplified CCD camera (12).

10. A method of detecting and/or controlling two-dimensional concentration and/or pressure distributions of process particles within a low pressure process chamber (2), which forms part of a semiconductor production device (1) and in the interior of which a vacuum below $10^{-2}$ mbar can be generated with the aid of a vacuum pump means, comprising the following steps:
    producing a substantially parallel light fan within the process chamber (2), the light fan penetrating the area of the process chamber (2) which is to be examined with regard to concentration distribution and/or pressure distribution, the power of a low power light fan source and the wavelength of the light emitted by the low power light fan source being so selected that the process particles have imparted thereto an excitation energy which causes a resonant fluorescent radiation;
    detecting the area to be examined by means of a camera (12), which is arranged such that its camera direction is disposed at an angel with respect to the light fan and the spectral sensitivity of which is so selected that, in the process particles, the camera has a quantum efficiency which suffices for detecting said fluorescent radiation;

splitting the light fan subsequent to the light fan source (5) in the light path;

detecting the intensity distribution of the light across the light fan; and determining the two-dimensional concentration and/or pressure distribution of the process particles by means of processing device (10), which is connected to the camera (12), said determination being carried out on the basis of image signals received by the processing device (10) from the camera (12) and on the basis of the detected intensity distribution.

* * * * *

UNITED STATES PATENT AND TRADEMARK OFFICE
CERTIFICATE OF CORRECTION

PATENT NO. : 5,153,674
DATED : October 6, 1992
INVENTOR(S) : FRIEDRICH BÖBEL
NORBERT BAUER It is certified that error appears in the above-indentified patent and that said Letters Patent is hereby corrected as shown below:

In the Cover Page:

In [73] Assignee:

change "Zur Forderung der angewandt" to
    -- zur Förderung der angewandten Forschung, e. V. --

Signed and Sealed this

Twenty-eighth Day of June, 1994

*Attest:*

BRUCE LEHMAN

*Attesting Officer    Commissioner of Patents and Trademarks*